United States Patent [19]

Komiya

[11] 4,038,987
[45] Aug. 2, 1977

[54] FORCEPS DEVICE FOR ENDOSCOPE

[75] Inventor: Osamu Komiya, Hachioji, Japan

[73] Assignee: Olympus Optical Co., Ltd., Tokyo, Japan

[21] Appl. No.: 546,929

[22] Filed: Feb. 4, 1975

[30] Foreign Application Priority Data

Feb. 8, 1974 Japan .................... 49-16219[U]

[51] Int. Cl.² ............................. A61B 17/28
[52] U.S. Cl. ................................... 128/321
[58] Field of Search .................. 128/321, 303.15

[56] References Cited

U.S. PATENT DOCUMENTS

| | | | |
|---|---|---|---|
| 86,016 | 1/1969 | Howell | 128/321 |
| 2,034,785 | 3/1936 | Wappler | 128/321 |
| 2,113,246 | 4/1938 | Wappler | 128/321 |
| 2,545,865 | 3/1951 | Wallace | 128/303.15 |
| 2,887,110 | 5/1959 | Roeschmann | 128/321 |
| 3,709,226 | 1/1973 | Santos | 128/321 X |
| 3,835,842 | 9/1974 | Iglesias | 128/303.15 X |
| 3,842,839 | 10/1974 | Malis et al. | 128/321 X |

*Primary Examiner*—Channing L. Pace

[57] ABSTRACT

The forceps device for an endoscope includes a toggle joint operated through a wire coupling by the wire operation. Said toggle joint has a pair of forceps levers whose forward end portions constitute an operating section and whose intermediate portions are pivotally supported, and a pair of links connected between the base ends of said pair of forceps levers and said wire coupling.

6 Claims, 10 Drawing Figures

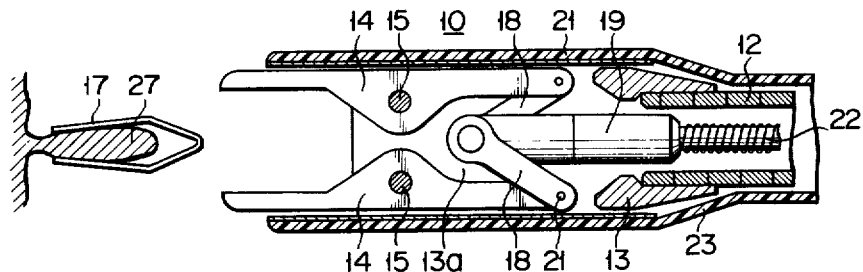
FIG. 4
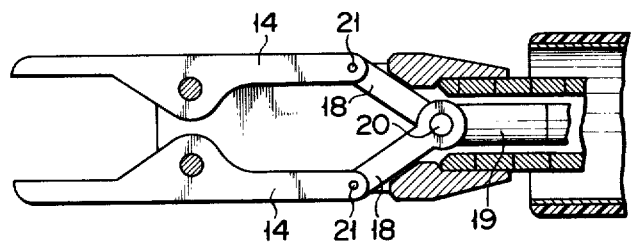
FIG. 5
FIG. 6     FIG. 9
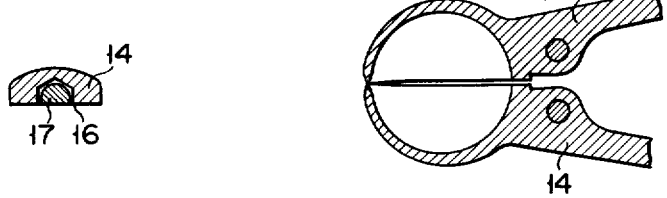
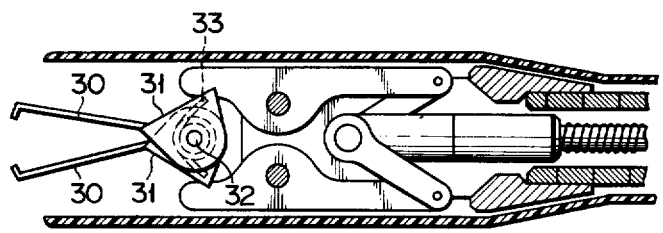
FIG. 10 or resect a deseased organ portion within a body cavity, or to insert into the body cavity and operate a grip for

FORCEPS DEVICE FOR ENDOSCOPE

BACKGROUND OF THE INVENTION

This invention relates to a forceps device for use in an endoscope, and more particularly to a foreceps device having a pair of forceps levers intended to hold or resect a deseased organ portion within a body cavity, or to insert into the body cavity and operate a grip for gripping a deseased organ portion desired to be resected.

In this type of forceps device, the forceps levers thereof are inserted through the endoscope into the body cavity and are operated from outside of the body. As such forceps device there is known the one having such a construction as illustrated, for example, in FIG. 1.

A pair of forceps levers 1, 2 whose forward end portions are cup-shaped are commonly privotally supported, at their intermediate portion, on the forward end portion of a forceps holder 3. The base end portions of the pair of forceps levers 1, 2 are connected to a wire coupling through a pair of links 5, 4, respectively. To the wire coupling 6 is connected one end of an operating wire 7. As a result, a parallel link mechanism is constituted by the paired forceps lever 1, 2 and links 4, 5 and when the wire coupling 6 has been drawn or pulled rearwardly to permit the link mechanism to be rendered flat, the forward ends of the forceps levers 1, 2 perform the holding or gripping function.

In the forceps device having the foregoing construction, the relationship of the tractive force 2F of the wire coupling 6 with the gripping force 2W of the forceps levers 1, 2 is expressed by the equation:

$$W = F\frac{r}{m} \sin\theta \left( \frac{l}{r} + \frac{\sqrt{1 - \left(\frac{l}{r}\right)^2 \sin^2\theta}}{\cos\theta} \right)$$

where $r$ represents the distance between a common pivot for the forceps levers 1, 2 and another common pivot for one of the forceps levers 1, 2 and a corresponding one of the links 4, 5; $m$ the distance between said common pivot and the forward end edge of the forceps levers; and $\theta$ is one half of the angle defined between the paired links 4 and 5. In an actual forceps device, the relationship of $l \approx r$ holds true. Accordingly, the above equation is rewritten as follows.

$$W \approx 2(r/m)\sin\theta$$

If it is assumed, therefore, that the tractive force be kept constant, the gripping force as applied by both forward ends of the forceps levers 1, 2 is maximum when $\theta = 90°$, and becomes smaller as the $\theta$ is rendered small.

It is, however, necessary for an actual device that when the paired forceps levers 1, 2 are brought into a closed condition, namely, when the $\theta$ is made minimum, then the gripping force at the forward ends of the forceps levers 1, 2 should be made maximum. Accordingly, in such conventional forceps device, a pulling or drawing force exerted upon the operating wire 7 fails to become a gripping force of the forceps levers with high efficiency, so that the pulling force loss is large. As a result, where it is desired to permit the forceps levers to carry out a prescribed gripping operation, a considerably large tractive force is required. For this reason, the operating wire has to be so formed thick as to resist such large tractive force and simultaneously the related parts or sections have to be formed firm, which renders the forceps device itself bulky.

SUMMARY OF THE INVENTION

The object of the invention is to provide a forceps device for use in an endoscope which is so constructed that the tractive force of the operating wire becomes a gripping force of the forceps levers with high efficiency, so that the gripping operation can be precisely carried out even when the device is miniaturized.

BRIEF DESCRIPTION OF THE DRAWING

FIGS. 2 to 5 are longitudinal sectional views schematically illustrating the tip end section of a forceps device according to an embodiment of the invention, and respectively illustrating the mutually different operative conditions of the forceps device;

FIG. 6 is a cross sectional view taken along the line 6—6 of FIG. 2;

FIG. 9 is a longitudinal section view illustrating a modification of the forceps of the tip end section; and FIG. 10 is a longitudinal sectional view illustrating a modification of a clip according to the invention.

DETAILED DESCRIPTION OF THE EMBODIMENTS

Figure 1:
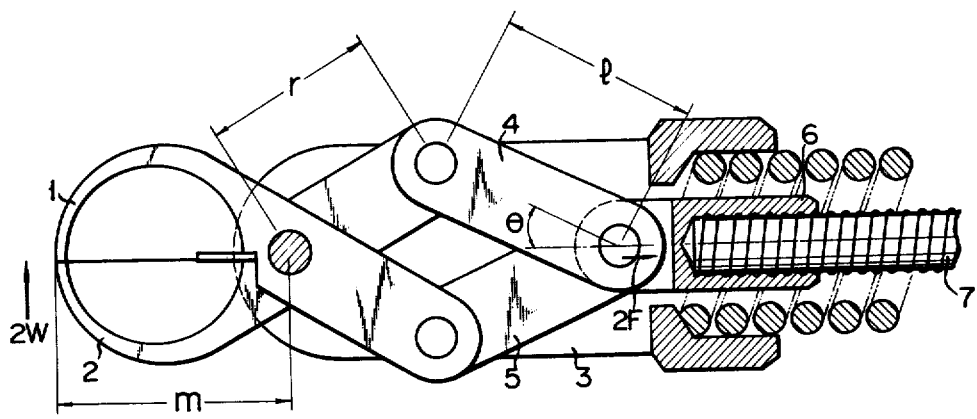
FIG. 1 is a longitudinal sectional view schematically illustrating a prior art forceps device.
Figure 2:
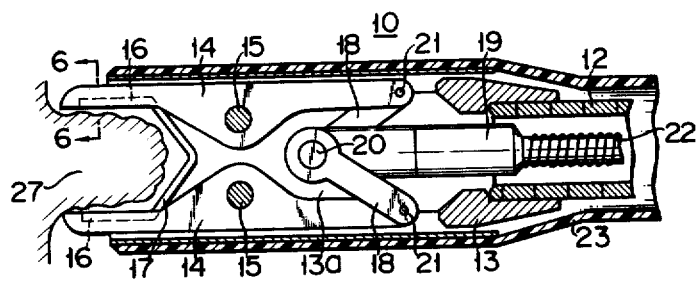

There will now be described a forceps device for use in an endoscope according to an embodiment of the invention by reference to FIGS. 2 to 7. The forceps device comprises a tip end section 10 extended into a human body cavity through the forceps opening of the endoscope to perform a desired clipping operation, an operating section 11 for operating the tip end section from outside of the human body, and an elongate, flexible outer tube 12 for connecting the tip end section 10 to the operating section 11. As illustrated in FIG. 2, the tip end portion 10 has a cylindrical forceps holder 13 coaxially attached to the forward end portion of the outer tube 12, the forward end portion of the forceps holder 13 constituting a pair of parallel extending support plates 13a which are spaced from each other at a prescribed interval. Between the pair of support plates 13a are provided a pair of forceps levers 14 in a manner that tne forceps levers 14 oppose each other and their respective intermediate protruded portions are pivotally supported on the pair of support plates 13a through pins 15. The outer side faces of the pair of forceps levers 14 are formed flat and are made parallel with each other, when the forceps levers are in an open-condition as illustrated in FIG. 2. The forward operating sections of the forceps levers 14 are forwardly extended from the forward sides of the support plates 13a and the inner faces, i.e., mutually opposing inner walls of said forward operating sections are formed with longitudinal elongate grooves 16. The forceps levers 14 are so designed that the forward end portions thereof sandwich a clip 17 and carry it into the body cavity to clip a deseased body portion with it. Mounting of the clip 17 onto the forceps levers 14 is carried out by inserting the parallel leg portions of the clip 17 into the elongate grooves 16 formed in the levers 14, as illustrated in FIG. 2. The clip 17 in this case is called a "hemoclip" as known in the art, which is formed of metal material having a substantially V-shape and plasticity.

Figure 3:
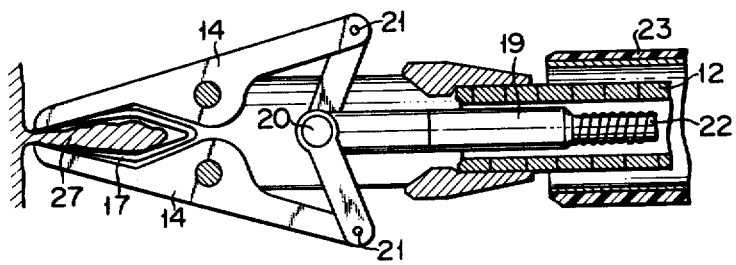

A pair of links 18 are pivotally supported at one end on the respective connecting end portions of the pair of forceps levers 14 through pins 21, and are pivotally coaxially supported at the other end on the forward end of a wire coupling 19 through a pin 20. The length of the link 18 is so determined that when the forceps levers 14 are in an opened condition as illustrated in FIG. 2, the pin 20 is not located on a line connecting both pins 21, whereas when the forceps levers 14 are in a closed condition as illustrated in FIG. 3, the pin 20 is located in, or in the proximity of, said line.

Figure 7:
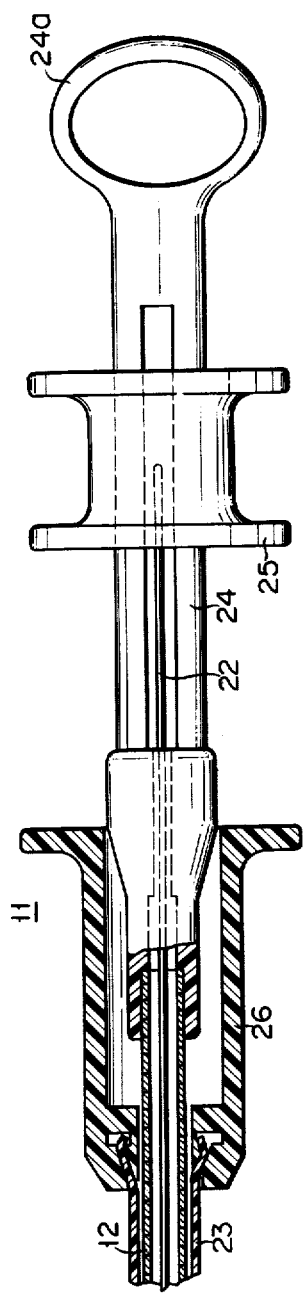
FIG. 7 is a longitudinal sectional view illustrating the operating section of the forceps according to said embodiment.
Figure 8:
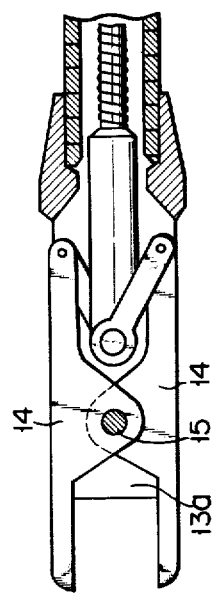
FIG. 8 is a longitudinal sectional view illustrating a modification of the tip end section of the forceps device according to the invention.

To the rearward end of the wire coupling 19 is connected the forward end of a tractive wire 22, the rearward end of which extends through and along outer tube 12 into the operating section 11 (FIG. 7). Outside the outer tube 12 is slidably provided along its longitudinal direction a guide tube 23, only the forward end portion of which is preferably formed rigid so as not to be deformed and the remaining portion of which is preferably formed flexible. In this embodiment, the guide tube 23 consists of a flexible synthetic resin tube and a metal tube mounted on the inner face of the forward end portion of the synthetic resin tube.

When the forceps levers 14 are in an open condition, the forward rigid end portion of the guide tube 23 is extended up to the vicinity of the forward ends of the forceps levers 14 to cover the outer faces of the forceps levers 14 and simultaneously to permit the forceps levers 14 to be kept parallel. In contrast, when the forceps levers 14 are in a closed condition, the guide tube 23 is rearwardly slided so as to cause the portion thereof to be located rearwardly of the forceps levers 14, thereby to permit the rocking operation thereof to be performed. The sliding operation of the guide tube 23 as well as the drawing operation of the tractive wire 22 is carried out outside the body through the operating section 11 (See FIG. 7) located at the control unit of the endoscope.

The operating section 11 of the forceps device includes a columnar fixed base body 24 having an operator's finger inserting ring portion 24a at its rear end. To the forward end of the base body 24 is connected the rearward end of the outer tube 12. Further, the base body 24 is provided with first and second sliding members 25 and 26 which are slidable along the longitudinal direction of the base body 24. To the first sliding member 25 is connected the rearward end of the tractive wire 22. To the second sliding member 26 is connected the rearward end of the guide tube 23. As a result, if the first member 25 is slided relative to the base body 24, the tractive wire 22 will be able to be longitudinally moved along the outer tube 12, while if the second member 26 is slided relative to the base body 24, the guide tube 23 will be able to be similarly longitudinally moved along the outer tube 12.

There will now be described the operation of the above-constructed forceps device in the case where a deseased portion of the human body is clipped with the hemoclip, using the conventional endoscope.

By sliding the first member 25 of the forceps device in a direction wherein the first member 25 goes away from the ring portion 24a, the pair of forceps levers 14 are brought into an open condition as illustrated in FIG. 2 to permit the forward end portions thereof to hold the hemoclip 17. The second member 26 is similarly forwardly moved to permit the forward end portion of the guide tube 23 to cover the forceps levers 14. The forceps device kept in such condition is inserted into the endoscope whose distal end has previously been inserted up to the proximity of the deseased portion within the body cavity, and the tip end section 10 of the forceps device is extended up to the deseased portion 27, thereby to allow it to be positioned between the pair of forceps levers 14. At this time, the deseased portion 27 is of course located between the opposed legs of the hemoclip 17 held in place by the forceps levers 14. Next, the second member 26 is drawn toward the ring portion 24a to permit the forward end portion of the guide tube 23 to be moved rearwardly of the pair of forceps levers 14, and simultaneously the first member 25 is also rearwardly drawn to permit the pair of forceps levers 14 to be so rocked as to cause both forward ends thereof to approach each other. Thus, the pair of forceps levers 14 are brought into a closed condition. By the rocking movement of the forceps levers 14 in a direction wherein both forward ends thereof approach each other, the hemoclip 17 supported therebetween is crushed to clip the deseased portion 27. The rocking movement of the forceps levers in this direction is performed as follows. The drawing of the first member 25 causes the wire coupling 19 to be rearwardly pulled through the tractive wire 22. As a result, both links 18 are moved in a direction intersecting the lengthwise direction of the wire coupling 19 substantially at right angles, namely, in a direction wherein the common pin 20 approaches the straight line connecting both pins 21. As a result, the rearward ends of the both forceps levers 14 are swung outwards. When the pair of forceps levers 14 have been brought into the most close condition that is, when the forward ends of both the forceps levers 14 have approached each other to a maximum extent, said both links 18 are placed at a position in which they intersect the lengthwise directon of the wire coupling 19 substantially at right angles thereto. At this time, therefore, the forward end portions of both the forceps levers 14 present the greatest gripping force. Namely, at this time, the pair of forceps levers 14, the pair of links 18 and the wire couplng 19 constitute a toggle joint. There results, accordingly, that the pair of forceps levers 14 have a gripping force extremely greater than the tractive force of the wire 22.

Since the aforesaid hemoclip 17 is plastically deformable, it remains to clip the deseased portion 27 even when the pair of forceps levers 14 have been brought back into the open condition. Where it is desired that the forceps levers 14 are returned to the open condition, the first and second members 25 and 26 have only to be returned to the original position.

Furthermore, if the links 18 and the forceps levers 14 are so designed that when the forceps levers 14 are in said most close condition, the common pin 20 is located on the straight line across both pins 21, that is, the three pins 20, 21 are located in the same plane, the forceps levers 14 will be brought to the open condition when the tractive wire 22 is further rearwardly pulled to cause the links 18 to be inclined forwardly. Since, in this case, the forceps levers 14 can be sequentially opened and closed only by one-directional sliding movement of the first member 25, the forceps device operation is more readily carried out.

As well known, the previously mentioned deseased organ portion 27 is allowed to stand in the clipped condition to death and is exfoliated jointly with the hemoclip 17 and then is eliminated from the body.

In the forceps device according to the preceding embodiment, the pair of forceps levers 14 are pivotally individually supported on the different positions of the support plate 13a through the pins 15, respectively. The pair of forceps levers 14, however, may be pivotally supported in common on the same part of the support plate 13a through a common pin 15. It will be understood, in this case, that the pair of forceps levers 14 are rendered rockable about the same axis as a fulcrum The clip 17 for use in the foregoing forceps device is not limited to the above-mentioned U-shaped wire clip alone, but such a clip as illustrated, for example, in FIG. 10 is also applicable. This clip 17 includes a pair of linear clip members 30, a pair of triangular plate-like bases 31 to which the base ends of the linear clip members 30 are fixed, respectively, a shaft 32 for pivotally supporting the bases 31, and a spring 33 for urging or biasing the pair of clip members 30 to rock them in their clipping direction.

When inserted into the body cavity, the forceps device is designed to hold the above clip 17 under the condition wherein the pair of forceps levers 14 are brought into an open condition to permit said bases 31 to be rocked against the biasing force of the springs 33.

The forceps of the present forceps device is not limited to the foregoing gripping forceps, but may be of any shape or construction if it has a pair of forceps levers which perform their function in such a mutually paired manner as in the case of the gripping or clipping function. The present forceps device is applicable also to a forceps having a gripping section in which the forward end portions of the paired forceps levers 14 are cup-shaped as illustrated, for example, in FIG. 9.

What is claimed is:

1. A forceps device to be inserted through an endoscope into a body cavity, comprising an outer covering tube, a forceps holder attached to one end portion of said outer covering tube, a pair of forceps levers each having operating end portions forming jaws, connecting end portions and intermediate portions therebetween pivotally supported on said forceps holder, means for operating said levers consisting of a pair of links each respectively pivotally connected to said one end of said connecting end portions of said forceps levers, a wire coupling pivotally connected to the other ends of said pair of links at a pivot point, and a wire having one end connected to said wire coupling and the other end extended through said outer covering tube, therealong, said pair of forceps levers and said pair of links constituting a toggle joint whereby when said wire coupling has been moved by pulling the same from its other end, said links are moved to a position approaching a substantially straight line drawn between the pivots connecting said forceps levers and links, and the pivot point of said wire coupling, said forceps levers being rocked through said links to permit said operating end portions of said levers to be moved in a clamping direction approaching each other.

2. A forceps device according to claim 1, wherein said operating end portions of said forceps levers have clip inserting grooves formed, respectively, in their mutually opposite faces.

3. A forceps device according to claim 1, wherein said operating forward end portions of said forceps levers have cup-shaped gripping sections.

4. A forceps device according to claim 1, which further comprises an outer guide tube having a forward end portion for selectively covering the outer side faces of said forceps levers and slidably disposed on the outside of said covering tube.

5. A forceps device according to claim 1, wherein said forceps levers are pivotally supported on said forceps holder about the same axis.

6. A forceps device according to claim 1, wherein said forceps levers pivotally supported on said forceps holder about different axes.

* * * * *